United States Patent
Runkana et al.

(10) Patent No.: US 11,043,286 B2
(45) Date of Patent: Jun. 22, 2021

(54) POLYMERIC CARRIERS FOR CONTROLLED RELEASE OF MOLECULES

(71) Applicant: Tata Consultancy Services Limited, Mumbai (IN)

(72) Inventors: Venkataramana Runkana, Pune (IN); Beena Rai, Pune (IN); Aditya Pareek, Pune (IN); Balarama Sridhar Dwadasi, Pune (IN); Rakesh Gupta, Pune (IN)

(73) Assignee: TATA CONSULTANCY SERVICES LIMITED, Mumbai (IN)

( * ) Notice: Subject to any disclaimer, the term of this patent is extended or adjusted under 35 U.S.C. 154(b) by 635 days.

(21) Appl. No.: 15/889,455

(22) Filed: Feb. 6, 2018

(65) Prior Publication Data

US 2018/0225425 A1 Aug. 9, 2018

(30) Foreign Application Priority Data

Feb. 9, 2017 (IN) .............................. 201721004772

(51) Int. Cl.
| | | |
|---|---|---|
| G06F 17/10 | (2006.01) | |
| G16C 20/10 | (2019.01) | |
| G16C 10/00 | (2019.01) | |
| G16C 20/50 | (2019.01) | |
| G16C 20/30 | (2019.01) | |
| G06F 111/10 | (2020.01) | |

(52) U.S. Cl.
CPC .............. G16C 20/10 (2019.02); G16C 10/00 (2019.02); G16C 20/50 (2019.02); *G06F 2111/10* (2020.01); *G16C 20/30* (2019.02)

(58) Field of Classification Search
CPC .......... G16C 10/00; G16C 20/10; G16C 20/50
USPC .............................................................. 703/2
See application file for complete search history.

(56) References Cited

U.S. PATENT DOCUMENTS 9,096,877 B2 * 8/2015 Johnson ............. C07K 16/2887
9,598,544 B2 * 3/2017 Jiang ..................... C07C 317/08
(Continued)

OTHER PUBLICATIONS

Bajpai et al. (Dynamics of controlled release of heparin from swellable crosslinked starch microspheres, 9 pages. (Year: 2007).*

(Continued)

*Primary Examiner* — Andre Pierre Louis
(74) *Attorney, Agent, or Firm* — Finnegan. Henderson, Garrett & Dunner, LLP

(57) ABSTRACT

A system and method for design of polymeric carrier for controlled release of molecules is provided. The method includes receiving a plurality of input parameters of a polymeric carrier, a solvent, and molecules to be released from the polymeric carrier from a database and performing Molecular Dynamics (MD) simulations to estimate thermodynamic and transport properties of the polymeric carrier, the solvent and the molecules to be released using on one or more input parameters from the plurality of input parameters. Based on the estimated thermodynamic and transport properties, swelling and degradation kinetics of the polymeric carrier and release kinetics of the molecules to be released from the polymeric carrier is estimated and generating a proposed formulation based on difference between estimated released kinetics and the targeted release kinetics of the molecules.

14 Claims, 4 Drawing Sheets

(56) References Cited

U.S. PATENT DOCUMENTS

2012/0064142 A1\* 3/2012 Pillay .................. A61K 9/5138
                                                          424/423
2012/0172456 A1   7/2012 Little et al.

OTHER PUBLICATIONS

Caccavo, D. et al. (2015). "Modeling the Drug Release from Hydrogel-Based Matrices," *American Chemical Society*; pp. 474-483.

Wishart, D.S. et al. (Jan. 2006). "DrugBank: a comprehensive resource for in silico drug discovery and exploration," *Nucleic Acids Research*, vol. 34, issue sup. 1; pp. D668-672.

\* cited by examiner

POLYMERIC CARRIERS FOR
CONTROLLED RELEASE OF MOLECULES

PRIORITY CLAIM

This U.S. patent application claims priority under 35 U.S.C. § 119 to: India Application No. 201721004772, filed on Feb. 9, 2017. The entire contents of the aforementioned application are incorporated herein by reference.

TECHNICAL FIELD

The present subject matter relates, in general, to controlled release of molecules, and, in particular, to design of polymeric carrier for controlled release of molecules.

BACKGROUND

Polymeric carriers such as polymer hydrogels are unique class of macromolecular networks that can hold a large fraction of water within their structures and are currently under research for applications in controlled delivery systems, tissue engineering, contact lenses, agricultural chemicals, cosmetics and food formulations and the like. Biodegradable polymer based microparticles, nanoparticles and fibers too hold similar potential, wherein polymer degradation facilitates controlled release of molecules. Deciding what formulation i.e. polymer, solvent, functional group and their composition to be used to achieve the desired release kinetics is a design problem. In practice, formulation scientists and polymer chemistry experts use their knowledge to narrow down on the limited set of polymers, solvents and important composition parameters of formulation, the combination of which may give the controlled release of molecule to be released. A rigorous design of experiment studies are carried out to compare the effect of formulation parameters on release kinetics and finally select the one that gives satisfactory results. This process is time and resource consuming since it requires not only the synthesis experiments but also release experiments for each possible set of formulation parameters. The results obtained may also usually do not guarantee success in terms of final design of the polymeric carrier based formulation.

SUMMARY

The following presents a simplified summary of some embodiments of the disclosure in order to provide a basic understanding of the embodiments. This summary is not an extensive overview of the embodiments. It is not intended to identify key/critical elements of the embodiments or to delineate the scope of the embodiments. Its sole purpose is to present some embodiments in a simplified form as a prelude to the more detailed description that is presented below.

In view of the foregoing, embodiments herein provide a systems and methods for providing multi-level data representation of object lifecycle. In one aspect, computer-implemented method executed by a computing device for design of polymeric carrier for controlled release of molecules is provided. The method receiving a plurality of input parameters of a polymeric carrier, a solvent, and molecules to be released from the polymeric carrier from a database, performing Molecular Dynamics (MD) simulations to estimate thermodynamic and transport properties of the polymeric carrier, the solvent and the molecules to be released using one or more input parameters from the plurality of input parameters, estimating swelling and degradation kinetics of the polymeric carrier and release kinetics of the molecules to be released from the polymeric carrier based on the estimated thermodynamic and transport properties of the polymeric carrier and molecules to be released via multi-physics simulations, comparing the estimated release kinetics with targeted release kinetics of the molecules to be released; and generating a proposed formulation based on difference between estimated released kinetics and the targeted release kinetics of the molecules, wherein the proposed formulation comprises parameters associated with the polymeric carrier and the solvent corresponding to the molecules to be released.

In another one aspect, a computer-implemented system for design of polymeric carrier for controlled release of molecules is provided. The system includes at least one memory and at least one processor. The at least one memory is coupled to the at least one processor is capable of executing programmed instructions stored in the at least one memory to receive a plurality of input parameters of polymeric carrier, a solvent, and molecules to be released from the polymeric carrier from a database, perform Molecular Dynamics (MD) simulations to estimate thermodynamic and transport properties of the polymeric carrier, the solvent and the molecules to be released using one or more input parameters from the plurality of input parameters, estimate swelling and degradation kinetics of the polymeric carrier and release kinetics of molecules to be released from the polymeric carrier based on the estimated thermodynamic and transport properties of the polymeric carrier and molecules to be released via multi-physics simulations, compare the estimated release kinetics with targeted release kinetics of the molecules to be released and generate a proposed formulation based on difference between estimated released kinetics and the targeted release kinetics of the molecules, wherein the proposed formulation comprises parameters associated with the polymeric carrier and the solvent corresponding to the molecules to be released.

In yet another aspect, a non-transitory computer-readable medium having embodied thereon a computer program for executing a method for design of polymeric carrier for controlled release of molecules is disclosed. The method includes receiving a plurality of input parameters of polymeric carrier, a solvent, and molecules to be released from the polymeric carrier from a database. The method further includes performing Molecular Dynamics (MD) simulations to estimate thermodynamic and transport properties of the polymeric carrier and the molecules to be released using one or more input parameters from the plurality of input parameters and estimating swelling and degradation kinetics of the polymeric carrier and release kinetics of molecules to be released from the polymeric carrier based on the estimated thermodynamic and transport properties of each of the plurality of input parameters of the polymeric carrier and molecules to be released via multi-physics simulations. Further, includes comparing the estimated release kinetics with targeted release kinetics of the molecules to be released; and generating a proposed formulation based on difference between estimated released kinetics and the targeted release kinetics of the molecules. The proposed formulation comprises parameters associated with the polymer carrier and the solvent corresponding to the molecules to be released.

It should be appreciated by those skilled in the art that any block diagram herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and so executed by a computing device or processor, whether or not such computing device or processor is explicitly shown.

BRIEF DESCRIPTION OF THE DRAWINGS

The embodiments herein will be better understood from the following detailed description with reference to the drawings, in which.

DETAILED DESCRIPTION

Figure 1:
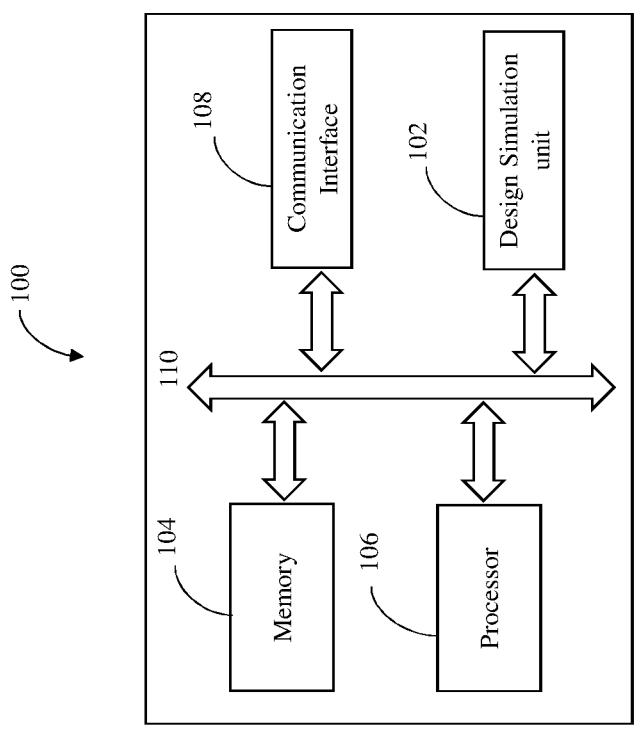
FIG. 1 illustrates a block diagram for design of polymeric carrier for controlled release of molecules, in accordance with an example embodiment.

The embodiments herein and the various features and advantageous details thereof are explained more fully with reference to the non-limiting embodiments that are illustrated in the accompanying drawings and detailed in the following description. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Referring now to the drawings, and more particularly to FIGS. 1 through 4, where similar reference characters denote corresponding features consistently throughout the figures, there are shown preferred embodiments and these embodiments are described in the context of the following exemplary system and/or method.

FIG. 1 is a block diagram of a system 100 for design of polymeric carrier for controlled release of molecules, in accordance with an example embodiment. The system 100 includes a design simulation unit 102 for design of polymeric carrier for controlled release of molecules. The design simulation unit may include one or more simulation tools molecular dynamics tool, multi-physics tool, optimization tool and the like. The design simulation unit 102 includes or is otherwise in communication with at least one memory such as a memory 104, at least one processor such as a processor 106, and a communication interface 108. The memory 104, processor 106, and the communication interface 108 may be coupled by a system bus such as a system bus 110 or a similar mechanism. Although FIG. 1 shows example components of design simulation unit 101, in other implementations, system 100 may contain fewer components, additional components, different components, or differently arranged components than depicted in FIG. 1.

The at least one processor such as the processor 106 may be implemented as one or more microprocessors, microcomputers, microcontrollers, digital signal processors, central processing units, state machines, logic circuitries, and/or any devices that facilitates in designing polymeric carrier for controlled release of molecules. Further, the processor 106 may comprise a multi-core architecture. Among other capabilities, the processor 106 is configured to fetch and execute computer-readable instructions or modules stored in the memory 104. The processor 106 may include circuitry implementing, among others, audio and logic functions associated with the communication. For example, the processor 106 may include, but are not limited to, one or more digital signal processors (DSPs), one or more microprocessor, one or more special-purpose computer chips, one or more field-programmable gate arrays (FPGAs), one or more application-specific integrated circuits (ASICs), one or more computer(s), various analog to digital converters, digital to analog converters, and/or other support circuits. The processor 106 thus may also include the functionality to encode messages and/or data or information. The processor 106 may include, among other things, a clock, an arithmetic logic unit (ALU) and logic gates configured to support operation of the processor 106. Further, the processor 106 may include functionality to execute one or more software programs, which may be stored in the memory 104 or otherwise accessible to the processor 106.

The memory 104, may store any number of pieces of information, and data, used by the system 100 to implement the functions of the system 100. The memory 104 may include any computer-readable medium known in the art including, for example, volatile memory, such as static random access memory (SRAM) and dynamic random access memory (DRAM), and/or non-volatile memory, such as read only memory (ROM), erasable programmable ROM, flash memories, hard disks, optical disks, and magnetic tapes. Examples of volatile memory may include, but are not limited to volatile random access memory (RAM). The non-volatile memory may additionally or alternatively comprise an electrically erasable programmable read only memory (EEPROM), flash memory, hard drive, or the like. The memory 104 may be configured to store information, data, applications, instructions or the like for enabling the system 100 to carry out various functions in accordance with various example embodiments. Additionally or alternatively, the memory 104 may be configured to store instructions which when executed by the processor 106 causes the system 100 to behave in a manner as described in various embodiments.

The communication interface(s) 108 can facilitate multiple communications within a wide variety of networks and protocol types, including wired networks, for example, local area network (LAN), cable, etc., and wireless networks, such as Wireless LAN (WLAN), cellular, or satellite. For the purpose, the communication interface (s) 108 may include one or more ports for connecting the design simulation unit 101. One or more functionalities of the system 100 and components thereof, is further explained in detail with respect to FIG. 2 and FIG. 3.

In one implementation of system and method for design of polymeric carrier for controlled release of molecules, the polymeric carrier is polymer hydrogel for controlled release of drug molecules, molecules having therapeutic value. In another implementation, the polymeric carrier may include but not limited to polymer particles, polymer gels and polymer fibers and the molecules to be released may include but not limited to bioactive agent, therapeutic agent, fertilizer, cosmetics, fragrance and anti-perspirant.

Figure 2:
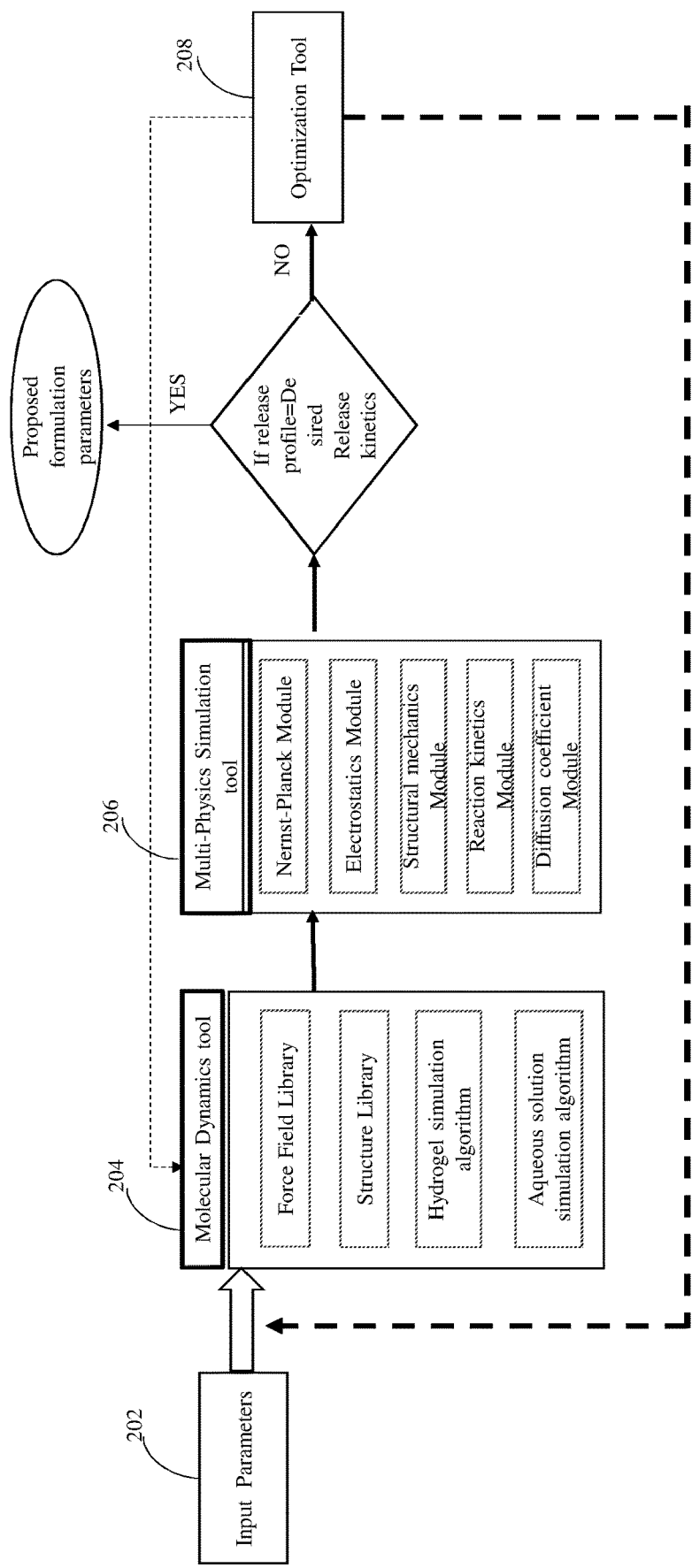
FIG. 2 illustrates a flow diagram of the design simulation unit of system FIG. 1, in accordance with an example embodiment.

Referring now to FIG. 2, in one implementation, the design simulation unit 102 may include a MD simulation tool 204, a multi-physics simulation tool 206 and an Optimization tool 208. A plurality of input parameters of a polymeric carrier, a solvent, and molecules be released from the polymeric carrier, are received at 202 from a knowledge database (not shown in the FIG). In an alternative embodiment the plurality of input parameters may be received by a user. The plurality of input parameters include formulation parameters, for example, but not limited to polymer volume fraction, solvent volume fraction, concentration of functional group, molecules to be released volume fraction and the like, solvent parameters, for example, chemical formula of solvent, chemical species present in the solvent, concentration of the chemical species, pH, temperature, ionic strength and the like, polymer parameters, for example, but not limited to polymer formula, polymer molecular weight, type of polymer, solubility of polymer and the like, carrier properties, for example, but not limited to shape, dimension, initial porosity, physical form of the carrier and the like, molecules to be released properties may include but not limited to chemical formula, solubility, size of molecule and the like.

The plurality of input parameters received from the database, for example a knowledge database are fed to the MD simulation tool 204. MD simulation is performed on the polymeric carrier, molecules to be released and the solvent to estimate thermodynamics and transport properties of the polymeric carrier and the molecules to be released. The transport properties of the polymeric carrier and the molecules to be released include diffusion coefficient, viscosity of the gel, and mesh area of the polymeric carrier. In an example embodiments the components of the MD simulation tool 204 are built using platforms, and not limited to, such as Material studio, LAMMPS and Gromacs.

The polymeric carrier may include but not limited to polymer particles, polymer gels and polymer fibers, the molecules to be released may include but not limited to a bioactive agent, a therapeutic agent, fertilizer, cosmetics, fragrance and anti-perspirant. In an example embodiment, the solvent may include organic and/or inorganic compounds.

The MD simulation tool 204, as shown in FIG. 2 includes one or more components, for example, a force field library containing the molecular interaction parameters of the solvent, cross-linkers, polymer and the molecule to be released, a structure library containing structures of the molecules to be released (i.e., co-ordinates of atoms of each molecule). The MD simulation tool 204 further comprises a polymeric carrier simulation and aqueous solution simulation algorithm to estimate the diffusion coefficient (transport property) and mesh area/size of the polymeric carrier.

In one implementation, the polymeric carrier simulation algorithm is used to estimate diffusion coefficient of drug molecule in hydrogel by the inputs received from the force field library and the structure library. In another implementation, the aqueous solution simulation algorithm is used to estimate diffusion coefficient of the drug molecule in an aqueous solution by the inputs received from force field and structure library.

In the polymeric carrier simulation algorithm, structure of the polymer in a simulation tool such as Gromacs or Materials studio is generated, for example, in here, structure of the polymer used to synthesize hydrogel is generated. The chains of the polymer are chemically cross-linked. The chemically cross-linked hydrogel based polymers are developed in two stages. In the first stage, an amorphous cell consisting two polymer chains, each containing specific number of monomers (that is based on molar mass of monomer and molecular weight of polymer) and required number of cross-linker molecules based on cross-linker concentration is developed using, for example, Accerlys Material Studio at lower density of the amorphous cell. In second stage, the polymers are allowed to cross-link by a cross-linking simulation. The cross-linking simulation is performed to identify the reactive sites of the polymer and cross linker and to form a bond between two nearby reactive sites of polymer and the cross-linker molecules. The process of identifying the reactive sites is repeated until all the reactive atoms are connected and thereby a network is formed by the connection of the reactive atoms. The network resulting from the cross-linking process is minimized and allowed to relax at high temperatures followed by minimization. In an example, a cross-link carrier mixture is prepared according to the equilibrium swelling of water (solvent) based on Flory-Rehner equation and drug molecules (molecules to be released) are added according to their solubility in water. In the case of diffusion of drug molecule in polymer hydrogel, the system consists of cross linked polymer, water and the drug molecules. MD simulations are performed on the mixture and diffusion coefficient is calculated using the equation [1].

$$\frac{\partial \langle r^2(t) \rangle}{\partial t} = 2dD \qquad [1]$$

Where, r denotes the position of the particles in Cartesian coordinates
t denotes time
d denotes the dimensionality (d=2 for two dimensional system, d=3 for three dimensional system.

In the aqueous solution simulation, water (solvent) and the drug molecules (molecules to be released) are received from the structure library to form a mixture. The MD simulation is performed on the mixture and mean square displacement is calculated from the trajectories generated in MD simulation. The diffusion coefficient is related to the mean square displacement presented in [1].

In general, the mixture are infinitely dilute i.e. concentration of molecules to be released is very low. Hence, it may be difficult to calculate diffusivities in short simulation times. Therefore, in one implementation, multiple MD simulations are performed to estimate the diffusion coefficient in the aqueous solution. Mean and error in diffusion coefficient is performed by boot strapping analysis with replacement, where a number of data sets are picked randomly and values of diffusion coefficient are calculated. These values are then used in calculation of mean and standard error in the estimate of diffusion coefficient.

The estimated thermodynamic and transport properties, that is the diffusion coefficient of the polymeric carrier and the molecules to be released by the MD simulation are fed to the multi-physics simulation tool 206 to estimate swelling kinetics of hydrogel and release kinetics of the molecules to be released. The MD simulation primarily includes output parameters such as the diffusion coefficient and mesh area of the hydrogel at a swollen state. The output properties are communicated between the MD tool 204 and multi-physics simulation tool 206 along with the other parameters.

The other parameters include the release environment parameters, for example, the environment in which the molecules to be released, and that carrier properties, namely shape and dimensions of polymeric carrier, herein for example, the polymeric carrier is polymer hydrogel, formulation parameters, namely concentration of functional group, drug molecules and polymer volume fraction is fed as the input parameter for multi-physics simulation tool 206.

Based on the release environment parameters and carrier properties, the swelling kinetics of polymer hydrogel based polymeric carrier and release kinetics of molecules to be released are estimated. In an example embodiment, the multi-physics simulation tool 206 may be built using software such as COMSOL Multi-physics and Ansys Fluent.

The multi-physics simulation tool 206 includes one or more modules, namely, Diffusion coefficient module, Nernst-Planck module, Electrostatics module, Structural mechanics module, Reaction kinetics module. In an example embodiment, the one or more modules are developed using COMSOL multi-physics. The modules may also be developed using other CFD software such as Ansys Fluent and the like. The parameters estimated by MD simulations are incorporated in multi-physics simulation. The diffusion coefficient of the molecules to be released, estimated by MD simulations, is utilized in multi-physics simulations for design of polymer hydrogel based polymeric carriers.

The MD simulations tool 204, communicate the calculated diffusion coefficients either at equilibrium swelling of hydrogel or in the release environment. Thus, the diffusion coefficient needs to be scaled at intermediate swelling of hydrogel. Therefore, the diffusion coefficient module is called upon to estimate the transport properties such as to estimate diffusion coefficients of the solvent, molecules to be released and other relevant molecules present in the release environment and in the polymeric carrier. At each time step of simulation, the estimated diffusion coefficient is applied in Nernst-Planck module to account for transport of one or more molecules including molecules to be released from hydrogel to the surrounding release environment and vice versa. The inputs for Nernst-Planck module is received from the diffusion coefficient module required to calculate diffusive fluxes of molecules, and electrostatics module in the form of electric potential. The electrostatics module estimates the electric potential, in case of an ionic hydrogel. Amount of deformation or swelling of the hydrogel is estimated by structural mechanics module. Thereon if the molecules be it cross-linker, or molecules present in the release environment, functional groups present in polymeric carrier or molecule to be released, are undergoing chemical reaction, Reaction kinetics module is called upon. The modules described here receive inputs from one or more modules and represent coupling that is two way flow of information. Also, the modules described here consists of set of equations that may be extended or in some cases simplified to simulate degradation of polymer particle, if polymer is degradable in nature, and release kinetics of molecules to be released from the polymeric carrier.

The diffusion coefficient module is called upon to estimate the transport properties such as estimate diffusion coefficients of the solvent, other relevant molecules present in the release environment interacting with the hydrogel such as ions, and the molecules to be released. In one embodiment the diffusion coefficient of the polymer is calculated at equilibrium swelling of the hydrogel using MD simulations. And, diffusion coefficient at intermediate swelling required for multi-physics simulation is estimated using a Fujita type correlation. Thereby the diffusivities estimated using MD simulation tool 204 is used for macroscopic level calculations performed by multi-physics simulation tool 206. Fujita's expression to estimate diffusivity at an intermediate swelling is shown in equation 2.

$$D_w^{gel} = D_w^{eq} \exp\left(-\beta_1\left(1 - \frac{v_w}{v_w^{eq}}\right)\right) \quad [2]$$

Where, $D_w^{gel}$ is diffusion coefficient of water in gel when volume fraction is water is $v_w$.

$D_w^{eq}$ is the diffusion coefficient at equilibrium water content or equilibrium swelling, $v_w^{eq}$, is estimated using Flory-Rehner equation.

$\beta_1$ is constant with values ranging from 2 to 6. Similar equation can be used to estimate diffusion coefficient of drug and other molecules free to diffuse in the gel.

In an alternative embodiment, diffusion coefficient is calculated in aqueous solution method using MD simulation. In the aqueous solution method, scaling law proposed by Lustig and Peppas is applied to estimate the diffusion coefficient of the molecule to be released at intermediate swelling of hydrogel using equation 3.

$$D_m^{gel} = D_m^w \left(1 - \frac{d_m}{\xi}\right) \exp\left(-\frac{1}{Q-1}\right) \quad [3]$$

Where, $D_m^{gel}$ is diffusion coefficient of a molecule in the gel phase at given swelling ratio $$Q = \frac{1}{1 - v_w}.$$

$D_m^w$ is diffusion coefficient of the same molecule in solvent phase, $d_m$ is the diameter of the molecule and $\xi$ is the mesh size of the polymer hydrogel given by equation 4.

$$\xi = Q^{\frac{1}{3}} CC_{length}\left(\frac{2C_n M_c}{M_0}\right)^{0.5} \quad [4]$$

Where, $CC_{length}$ is the length of C—C bond (can be anything else depending on the bond length of the repeating unit in the polymer) and $C_n$ is flory's characteristic ratio accounting for non-linear nature of a polymer chain.

In an alternative embodiment, the diffusion coefficient in the hydrogel, given diffusion coefficient in water, is estimated by conventionally known obstruction model and given by equation [5].

$$\frac{D_m^{gel}}{D_m^w} = \left(\frac{H}{2+H}\right)^2 \quad [5]$$

$$H = \frac{V_f - V_i}{V_i} = Q - 1 \quad [6]$$

Where, H is hydration state of the hydrogel which is ratio of increase in volume of the gel to the initial volume of the gel.

Further, spatial distribution of electric potential in the hydrogel is estimated using electrostatics module. The flux of ionic molecules estimated under the influence of electric potential by the electrostatic module is fed as an input to the Nernst-Planck module. Inputs for the electrostatic module is obtained in the form of concentration of all the ionic molecules present in the hydrogel from Nernst-Planck module as shown in equation [7]. In an example embodiment, a pH sensitive hydrogels surrounded by a salt solution of NaCl, the Nernst-Planck module estimates the concentration of ionic molecules, $c_k$, in the hydrogel and passes the concentrations of the molecules to electrostatics module.

The concentration of the molecules is used to estimate the total charge density present in the hydrogel.

$$\frac{\partial^2 \Psi}{\partial x^2} = -\frac{F}{\epsilon \epsilon_0}\left(\sum_{k=1}^{N} z_k c_k + z_f c_f\right) \quad [7]$$

Where, $\Psi$ is electric potential developed inside the gel phase, $c_k$ is concentration of ionic species such as Na+, Cl− and H+, $c_f$ is the concentration of ionized groups present in the ionic hydrogel which is estimated from equation 8 and 9 depending on the type of hydrogel.

$$c_f = \frac{1}{H}\frac{c_{mo}^s K}{(K + c_{H^+})} \text{ For anionic hydrogels} \quad [8]$$

$$c_f = \frac{1}{H}\frac{c_{mo}^s c_{H^+}}{(K + c_{H^+})} \text{ For cationic hydrogels} \quad [9]$$

Where, H, is the hydration state of the hydrogel. $c_{mo}^s$ is the initial concentration of ionizable groups present in the polymer chain and K is the dissociation constant of weak acid or base, and $C_{H^+}$ is the concentration of H+.

Flux of neutral and ionic molecules in the hydrogel is estimated by Nernst-Planck module. Transport of neutral molecules is influenced by concentration gradient only. Hence the concentration profile and thus release kinetics can be estimated using equation [10].

$$\frac{\partial c_i}{\partial t} + \nabla \cdot \left(-D_i^{gel} \nabla c\right) = 0 \quad [10]$$

Where, $c_i$ is concentration of any neutral molecules and $D_i^{gel}$ is diffusion coefficient in the gel phase estimated using diffusion coefficient module.

The concentration of ionic molecules is estimated at each time step of the multi-physics simulation using input of electric potential from electrostatics module and diffusion coefficient from the diffusion coefficient module. The final form of the equation is given by equation 11.

$$\frac{\partial c_i}{\partial t} + \nabla \cdot \left(-D_i^{gel} \nabla c_i - z_i \mu_{m,i} F c_i \nabla V\right) = \nu_i R \quad [11]$$

Where, $c_i$ is molar concentration of any ionic molecule (such as Na+, Cl−, H+); $D_i^{gel}$=Diffusion coefficient in the gel phase estimated using diffusion coefficient module, $\mu_{m,i}$ is ionic mobility ($\mu_{m,i}=D_i^{gel}/RT$) and F is Faraday's constant.

In an example, the polymeric carrier may consist of a reactive functional group or the polymer itself is capable to undergo reaction with the release environment and this influences the release of molecules. In such cases chemical reaction kinetics, R, need to be included which is estimated by a reaction kinetics module. The chemical reaction kinetics, R, is applied, in a case if the polymeric carrier includes one or more reactive groups. For example, polymers particles or fibers synthesized from polymers which are degradable in nature such as Poly-lactic acid (PLA) or Poly-lactic-glycolic acid (PLGA) require reaction kinetics module for prediction of mass-loss and change in molecular weight due to degradation.

In case of polymer hydrogel, reaction kinetics is accounted if the swelling behavior of the hydrogel is influenced by presence of reactive functional group or reactive molecule on polymer chains. One such example is of glucose responsive hydrogel, where enzymes such as glucose oxidase and catalase are immobilized on the polymer hydrogel. These enzymes react with glucose present in the release environment which lead to the formation of gluconic acid that causes ionization of charged groups present in the hydrogel and thus leading to swelling of the hydrogels. The rate expression is given in equation [12]. The rate expression shows rate of gluconic acid formation due to oxidation of glucose.

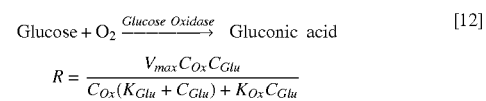

$$R = \frac{V_{max} C_{Ox} C_{Glu}}{C_{Ox}(K_{Glu} + C_{Glu}) + K_{Ox} C_{Glu}}$$

The rate expression shows rate of gluconic acid formation due to oxidation of glucose.

Where, $V_{max}$, $K_{Glu}$ and $K_{Ox}$ are reaction constants for Michaelis-Menten kinetics type reactions. $C_{Ox}$ is the concentration of oxygen and $C_{Glu}$ is concentration of glucose. The Reaction rates are laid out as described in the above example. Also, the user may enter the details of order of reaction, participating species and rate parameters to activate the reaction kinetics module.

The mesh size or hydration at intermediate swelling of hydrogel is estimated, by the changes in the structure of polymeric carrier at macro-scale level. This is required for estimating diffusion coefficient at intermediate swelling as explained previously in obstruction and scaling models. Displacement vector of the polymeric carrier from the initial configuration is estimated by the structural mechanics module. The displacement in the polymeric carrier is brought about by some driving force. For example of pH sensitive hydrogels, osmotic pressure is the swelling force which is opposed by elastic nature of the polymer chains present in the gel. A mechanical deformation equation given in equation [13] is used to estimate displacement vector, u, of pH sensitive hydrogel from its initial configuration.

$$\rho \frac{\partial^2 u}{\partial t^2} - \nabla \sigma = \nabla P_{osmotic} \quad [13]$$

$$\nabla \sigma = \nabla \cdot [\lambda(tr(E)I + 2\mu E - p_{osmotic} I] \quad [14]$$

$$P_{osmotic} = RT \sum (c_k - c_k^0) \quad [15]$$

Where, $\rho$ is the density of the hydrogel, $P_{osmotic}$ is osmotic pressure and $c_k^0$ is the salt concentration in the bulk phase. $\lambda$ and $\mu$ are two lame' elastic constants associated with Shear Modulus, G, Modulus of elasticity, E and Poisson's ratio $\nu$ as follows:

$$\lambda = \frac{\nu E}{(1+\nu)(1-2\nu)} \quad [16]$$

$$\mu = G = \frac{E}{2(1+\nu)} \quad [17]$$

The combination of MD simulation tool 204 and multi-physics simulation tool 206 estimates the release kinetics for the initial set of the one or more input parameters that corresponds to an initial predicted/proposed formulation. This initial proposed formulation may be optimized in conjunction with an optimization tool 208 such that the predicted release kinetics matches the targeted/desired release kinetics. The optimization tool 208 interacts with the MD simulations tool 204 and multi-physics simulations tool 206 simultaneously to generate an optimized formulation such that desired/targeted release rate is achieved from the polymeric carrier.

Figure 3:
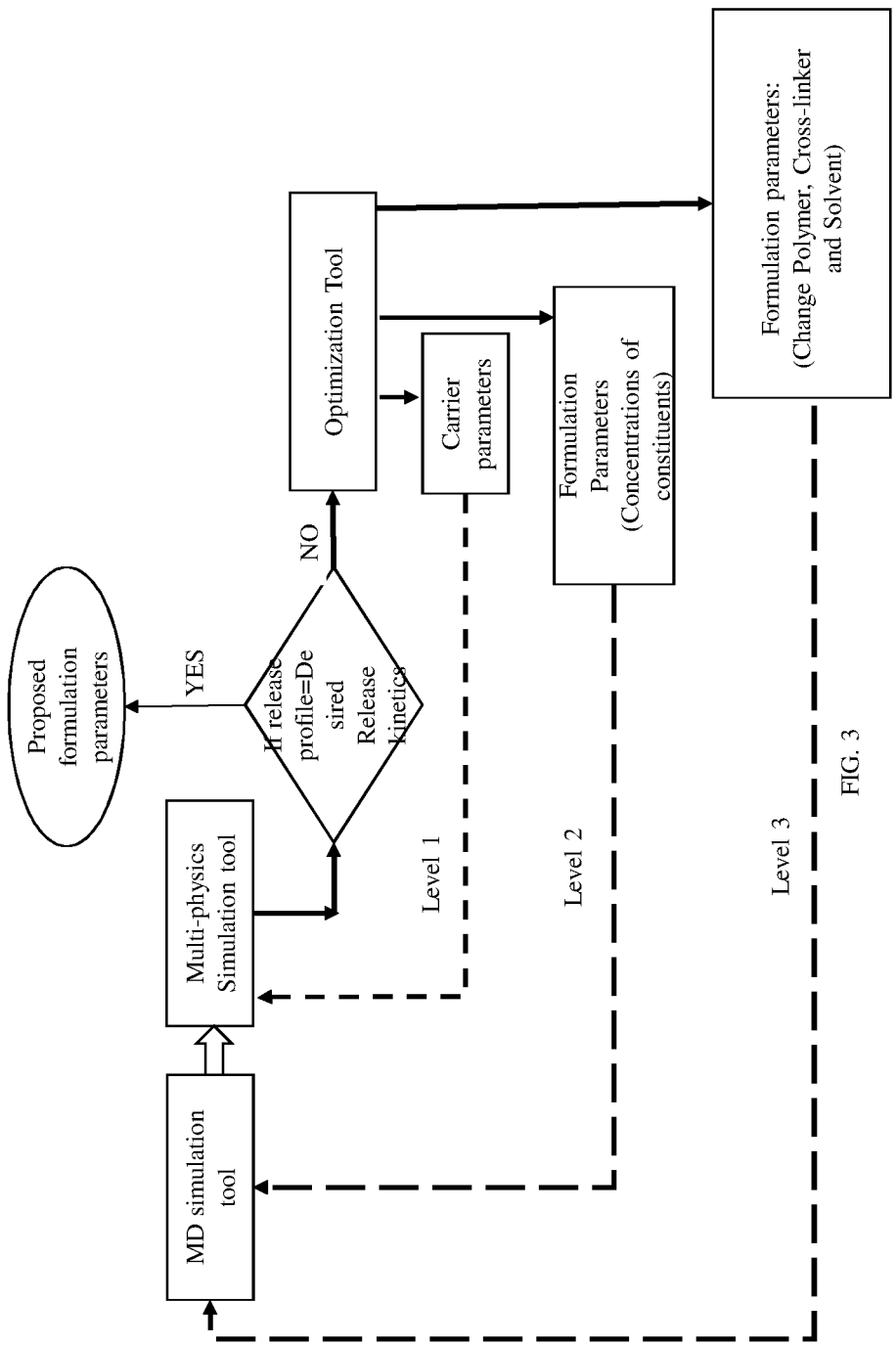
FIG. 3 illustrates an optimization tool of the design simulation unit FIG. 2, in accordance with an example embodiment.

FIG. 3 illustrates the detailed working principle of the optimization tool 208 of FIG. 2. The optimization tool of FIG. 3 is described with respect to obtain an optimal design of hydrogel based carrier. The optimization tool is called upon when the difference between the estimated release kinetics of the molecules to be released and the desired release kinetics is significant and/or above the defined tolerance limit. The optimization of the proposed formulation parameters is obtained by modifying the one or more input parameters from the plurality of input parameters of the polymer carrier and the solvent such that the targeted release rate of the molecules is achieved. Modifying the one or more input parameters may include carrier properties of the polymeric carrier and feeding the modified properties to the multi-physics simulations and formulation parameters of the polymeric carrier and feeding the modified formulation parameters to the MD simulations.

The optimization is performed at three different levels. At first level, the carrier properties such as shape and dimension of the polymeric carrier are modified within defined permissible limits and fed back to multi-physics simulations tool. Based on the modified parameters via multi-physics simulations tool, release kinetics of drug (molecules to be released) is estimated gain. If the first level of optimization does not generate a desired/targeted output, then second level of the optimization is called upon. At the second level the formulation parameters corresponding to the composition of the polymeric carrier such as polymer and cross-linker concentration are altered and fed back to the MD simulations as an input. The third level of optimization is called upon when first and second level fail to deliver desired release kinetics. In the third level of optimization, polymer, cross-linker and solvent or any combination thereof are fed back to the MD simulations tool and the release kinetics is estimated as described in FIG. 2.

As shown in FIG. 3, the optimization tool is stopped at any of the aforementioned levels when the proposed formulation parameters are achieved, that is, the difference between simulated and desired release kinetics is less than the defined tolerance limit. The multi-level optimization methodology ensures optimal formulation of the polymeric carrier and the solvent to achieve the desired/targeted rate of the molecules to be released.

Figure 4:
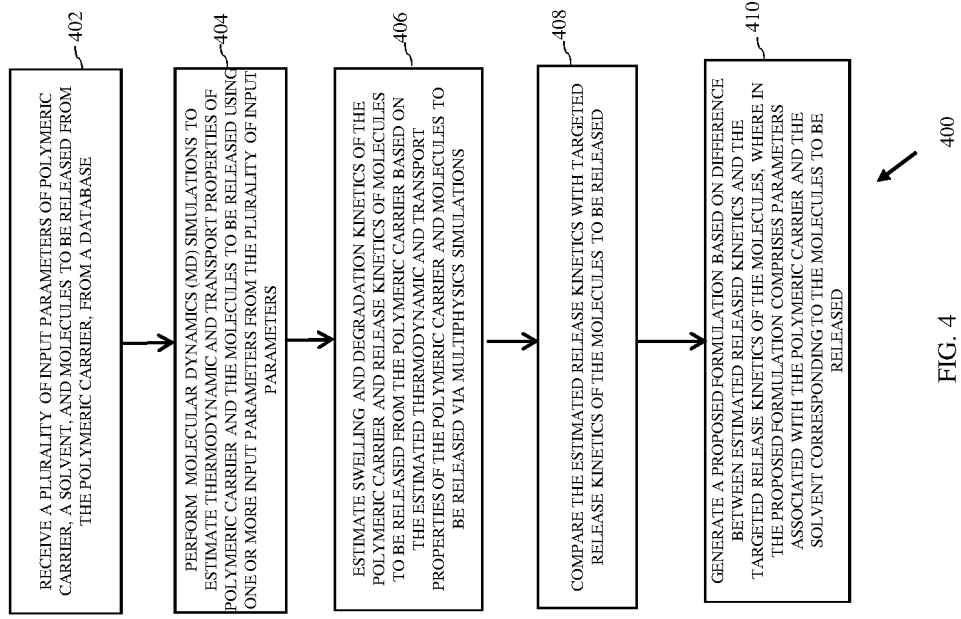
FIG. 4 illustrates a flow chart for design of polymeric carrier for controlled release of molecules, in accordance with an example embodiment.

FIG. 4 illustrates a flow diagram of a method 400 for design of polymeric carrier for controlled release of molecules, in accordance with the present disclosure. At block 402, molecular information of a plurality of input parameters of polymer carrier and molecules to be released from the polymer carrier, from a database is received. At block, 404, Molecular Dynamics (MD) simulations are performed to estimate thermodynamic and transport properties of polymeric carrier and molecules to be released. The thermodynamic and transport properties are estimated by obtaining molecular interaction parameters of the polymer carrier, the solvent and the molecules to be released from the database and based on the molecular interaction parameters the transport properties of the molecules to be released present in the polymeric carrier based is estimated. At block 406, multi-physics simulations are performed based on the thermodynamic and transport properties estimated by MD simulations to estimate swelling and degradation kinetics of polymeric carrier and release kinetics of molecules to be released from the polymer carrier. The swelling kinetics and degradation kinetics of the polymeric carrier along with release kinetics of molecules to be released is assessed by solving Nernst-Planck equation, Poisson equation and Force Balance equation, and reaction-diffusion equation in a coupled framework. Further, at block 408, the released kinetics is compared with a targeted release rate of the molecules to be released. At block 410, a proposed formulation is determined based on difference between estimated released kinetics and the targeted release kinetics of the molecules to be released. The proposed formulation includes parameters associated with the polymeric carrier and the solvent corresponding to the molecules to be released.

The method further includes modifying the one or more input parameters from the plurality of input parameters of the polymer carrier and the solvent such that the targeted release rate of the molecules is achieved. The modifying of the one or more input parameters may include altering carrier properties of the polymeric carrier and feeding the altered properties to the multi-physics simulations or formulation parameters of the polymeric carrier and feeding the altered formulation parameters to the MD simulations.

The order in which the in which the method(s) are described is not intended to be construed as a limitation, and any number of the described method blocks can be combined in any order to implement the method 400, or an alternative method. Additionally, individual blocks may be deleted from the methods without departing from the spirit and scope of the subject matter described herein. Furthermore, the method 400 can be implemented in any suitable hardware, software, firmware, or combination thereof.

In an implementation, one or more of the method(s) described herein may be implemented at least in part as instructions embodied in a non-transitory computer-readable medium and executable by one or more computing devices. In general, a processor (for example a microprocessor) receives instructions, from a non-transitory computer-readable medium, for example, a memory, and executes those instructions, thereby performing one or more method(s), including one or more of the method(s) described herein. Such instructions may be stored and/or transmitted using any of a variety of known computer-readable media.

In various embodiments of FIGS. 1-4, a method and system for design of polymeric carrier for controlled release of molecules is disclosed. Provides a protocol and tool for design of polymer based carriers for controlled release. The method disclosed comprises molecular dynamics and multi-physics simulations to reduce the number of trials or experiments conducted for designing polymeric carrier for controlled release of molecules to be released.

The present disclosure is a multi-scale modeling framework to predict release kinetics of molecules from a polymeric carrier. The method combines multi-scale simulation techniques namely Molecular Dynamics (MD) and Multi-physics simulations. MD focuses on phenomena at nanometer or smaller length scale and a similar time scale too (of the order of nanoseconds). And, the multi-physics simulations is focused at phenomena taking place at macro-scale (micro-meter or much larger) and longer time scales (minutes to days in case of release or swelling kinetics). The multi-scale framework when combined with optimization tool can be used for in-silico design of polymeric carrier that can achieve a desired release rate of molecules.

The proposed method and system of multi-scale framework has been validated against conventionally known experimental results in the art.

It is, however to be understood that the scope of the protection is extended to such a program and in addition to a computer-readable means having a message therein; such computer-readable storage means contain program-code means for implementation of one or more steps of the method, when the program runs on a server or mobile device or any suitable programmable device.

The preceding description has been presented with reference to various embodiments. Persons having ordinary skill in the art and technology to which this application pertains appreciate that alterations and changes in the described structures and methods of operation can be practiced without meaningfully departing from the principle, spirit and scope.

The invention claimed is:

1. A computer implemented method comprising:
   receiving a plurality of input parameters of a polymeric carrier, a solvent, and molecules to be released from the polymeric carrier, from a database, wherein the database further comprises molecular interaction parameters of the polymer carrier, the solvent and the molecules to be released from the polymeric carrier, and wherein plurality of input parameters corresponds to an initial proposed formulation;
   performing Molecular Dynamics (MD) simulations on one or more input parameters of the received plurality of input parameters, to estimate thermodynamic and transport properties of the polymeric carrier and the molecules to be released from the polymeric carrier, based on the molecular interaction parameters present in the database, wherein the transport properties include diffusion coefficient of the molecules to be released from the polymeric carrier, viscosity of the polymeric carrier, and mesh area of the polymeric carrier;
   performing multi-physics simulations on the estimated thermodynamic and transport properties of the polymeric carrier and the molecules to be released from the polymeric carrier, to estimate swelling and degradation kinetics of the polymeric carrier and release kinetics of the molecules to be released from the polymeric carrier based on release environment parameters and carrier properties;
   comparing the estimated release kinetics with targeted release kinetics of the molecules to be released from the polymeric carrier; and
   generating, in combination with the MD simulations and multi-physics simulations, an optimized formulation for the initial proposed formulation based on difference between the estimated release kinetics and the targeted release kinetics of the molecules, wherein the optimized formulation is generated by modifying the one or more input parameters from the plurality of input parameters of the polymer carrier and the solvent, in a plurality of levels, such that the targeted release kinetics of the molecules is achieved.

2. The method of claim 1, wherein modifying the one or more input parameters comprises altering at least one of:
   carrier properties of the polymeric carrier and feeding the altered properties to the multi-physics simulations; and
   formulation parameters of the polymeric carrier and feeding the altered formulation parameters to the MD simulations.

3. The method of claim 1, wherein the plurality of the input parameter comprises formulation parameters of the polymeric carrier, carrier properties of the polymeric carrier, chemical and physical properties of the molecules to be released and release environment.

4. The method of claim 1, wherein the multi-physics simulations comprises:
   obtaining from the MD simulations, the estimated transport properties and thermodynamic properties of the polymeric carrier, the solvent and the molecule to be released from the polymeric carrier;
   assessing the swelling kinetics of the polymeric carrier by combining Nernst-Planck equation, Poisson equation and Force Balance equation;
   assessing the degradation kinetics of the polymeric carrier using reaction-diffusion equations; and
   simulating the molecules to be released from the polymeric carrier.

5. The method of claim 1, wherein the polymeric carrier comprises one of polymer particles, polymer gels and polymer fibers.

6. The method of claim 1, wherein the molecules to be released from the polymeric carrier comprises one of a bioactive agent, a therapeutic agent, a fertilizer, cosmetics, a fragrance and an anti-perspirant.

7. The method of claim 1, wherein the solvent comprises one of organic and inorganic compounds.

8. A system comprising:
   at least one memory; and
   at least one processor, the at least one memory and a visualization interface coupled to the at least one processor, wherein the at least one processor is capable of executing programmed instructions stored in the at least one memory to:
   receive a plurality of input parameters of a polymeric carrier, a solvent, and molecules to be released from the polymeric carrier, from a database, wherein the database further comprises molecular interaction parameters of the polymer carrier, the solvent and the molecules to be released from the polymeric carrier, and wherein plurality of input parameters corresponds to an initial proposed formulation;
   perform Molecular Dynamics (MD) simulations on one or more input parameters of the received plurality of input parameters, to estimate thermodynamic and transport properties of the polymeric carrier and the molecules to be released from the polymeric carrier, based on the molecular interaction parameters present in the database, wherein the transport properties include diffusion coefficient of the molecules to be released from the polymeric carrier, viscosity of the polymeric carrier, and mesh area of the polymeric carrier;
   perform multi-physics simulations on the estimated thermodynamic and transport properties of the polymeric carrier and the molecules to be released from the polymeric carrier, to estimate swelling and degradation kinetics of the polymeric carrier and release kinetics of the molecules to be released from the polymeric carrier based on release environment parameters and carrier properties;
   compare the estimated release kinetics with targeted release kinetics of the molecules to be released from the polymeric carrier; and
   generate in combination with the MD simulations and multi-physics simulations, an optimized formulation for the initial proposed formulation based on difference between the estimated release kinetics and the targeted release kinetics of the molecules, wherein the optimized formulation is generated by modifying the one or more input parameters from the plurality of input parameters of the polymer carrier and the solvent, in a plurality of levels, such that the targeted release kinetics of the molecules is achieved.

9. The system of claim 8, wherein modifying the one or more parameters comprises altering at least one of:
   carrier properties of the polymeric carrier and feeding the altered properties to the multi-physics simulations; and
   formulation parameters of the polymeric carrier and feeding the altered formulation parameters to the MD simulations.

10. The system of claim 8, wherein the plurality of the input parameter comprises formulation parameters of the polymeric carrier, carrier properties of the polymeric carrier, chemical and physical properties of the molecules to be released and release environment.

11. The system of claim 8, wherein multi-physics simulations comprises:
   obtaining from the MD simulations, the estimated transport properties and thermodynamic properties of the polymeric carrier, the solvent and the molecule to be released from the polymeric carrier;
   assessing the swelling kinetics of the polymeric carrier by combining Nernst-Planck equation, Poisson equation and Force Balance equation;
   assessing the degradation kinetics of the polymeric carrier using reaction-diffusion equations; and
   simulating the molecules to be released from the polymeric carrier.

12. A non-transitory computer-readable medium having embodied thereon a computer program, the computer program being executed by a processor to perform a method comprising:
   receiving a plurality of input parameters of a polymeric carrier, a solvent, and molecules to be released from the polymeric carrier, from a database, wherein the database further comprises molecular interaction parameters of the polymer carrier, the solvent and the molecules to be released from the polymeric carrier, and wherein plurality of input parameters corresponds to an initial proposed formulation;
   performing Molecular Dynamics (MD) simulations on one or more input parameters of the received plurality of input parameters, to estimate thermodynamic and transport properties of the polymeric carrier and the molecules to be released from the polymeric carrier, based on the molecular interaction parameters present in the database, wherein the transport properties include diffusion coefficient of the molecules to be released from the polymeric carrier, viscosity of the polymeric carrier, and mesh area of the polymeric carrier;
   performing multi-physics simulations on the estimated thermodynamic and transport properties of the polymeric carrier and the molecules to be released from the polymeric carrier, to estimate swelling and degradation kinetics of the polymeric carrier and release kinetics of the molecules to be released from the polymeric carrier based on release environment parameters and carrier properties;
   comparing the estimated release kinetics with targeted release kinetics of the molecules to be released from the polymeric carrier; and
   generating, in combination with the MD simulations and multi-physics simulations, an optimized formulation for the initial proposed formulation based on difference between the estimated release kinetics and the targeted release kinetics of the molecules, wherein the optimized formulation is optimized generated by modifying the one or more input parameters from the plurality of input parameters of the polymer carrier and the solvent, in a plurality of levels, such that the targeted release kinetics of the molecules is achieved.

13. The non-transitory computer-readable medium of claim 12, wherein modifying the one or more input parameters comprises altering at least one of:
   carrier properties of the polymeric carrier and feeding the altered properties to the multi-physics simulations; and
   formulation parameters of the polymeric carrier and feeding the altered formulation parameters to the MD simulations.

14. The non-transitory computer-readable medium of claim 12, wherein the multi-physics simulations comprises:
   obtaining from the MD simulations, the estimated transport properties and thermodynamic properties of the polymeric carrier, the solvent and the molecule to be released from the polymeric carrier;
   assessing the swelling kinetics of the polymeric carrier by combining Nernst-Planck equation, Poisson equation and Force Balance equation;
   assessing the degradation kinetics of the polymeric carrier using reaction-diffusion equations; and
   simulating the molecules to be released from the polymeric carrier.

* * * * *